United States Patent [19]

Bommer et al.

[11] Patent Number: 4,675,338
[45] Date of Patent: Jun. 23, 1987

[54] TETRAPYRROLE THERAPEUTIC AGENTS

[75] Inventors: Jerry C. Bommer, Ogden; Bruce F. Burnham, Logan, both of Utah

[73] Assignee: Nippon Petrochemicals Co., Ltd., Tokyo, Japan

[21] Appl. No.: 631,925

[22] Filed: Jul. 18, 1984

[51] Int. Cl.⁴ .................... A61K 31/40; C07D 487/22
[52] U.S. Cl. ...................... 514/410; 514/2; 540/145
[58] Field of Search ............... 260/245.91, 112.5 R, 260/244.4; 514/410, 2, 372, 410; 424/2; 540/145

[56] References Cited

U.S. PATENT DOCUMENTS 4,393,071  7/1983  Fujii et al. ................... 424/274

FOREIGN PATENT DOCUMENTS 2850676  3/1976  Japan.
WO84/01382  4/1984  PCT Int'l Appl..

OTHER PUBLICATIONS

Cariello et al, Chemical Abstracts, vol. 90 (1979) 83836j.
Ballantine et al, Chemical Abstracts, vol. 93 (1980) 183058n.
Selve et al, Chemical Abstracts, vol. 95 (1981) 132,845a.
Jackson et al, Chemical Abstracts, vol. 97 (1982) 144645q.
Tsvetkov et al, Chemical Abstracts, vol. 101 (1984) 110,106a.
Fukuda et al, Chemical Abstracts, vol. 102 (1984) 122538y.
Chemical Berischte, 90, 470–481, 1957, by Lautsch, et al.
Hoppe-Seyler's Ztschr. Phy Chem., 327, 205–216, 1962, by Losse and Muller.
Chimia, 13, 129–180, 1959, by Karrer.
Tetrahedron Letters, 23, 2017–2020, 1978, by Pelter, et al.

(List continued on next page.)

Primary Examiner—Richard L. Raymond
Attorney, Agent, or Firm—Scully, Scott, Murphy & Presser

[57] ABSTRACT

The present invention relates to compounds having the following formula:

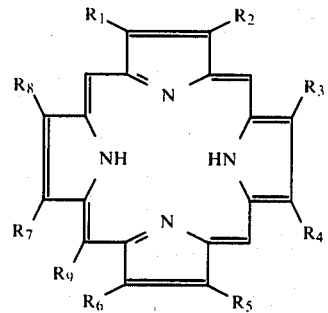

or the corresponding di- or tetrahydrotetrapyrroles wherein $R_1$ is methyl: $\begin{pmatrix} -H \\ -CH_3 \end{pmatrix}$ or $\begin{pmatrix} -OH \\ -CH_3 \end{pmatrix}$;

$R_2$ is H, vinyl, ethyl, $-CHCH_3$, acetyl, $\begin{pmatrix} -H \\ -ethyl \end{pmatrix}$,
     |
     OH $\begin{matrix} H \\ | \\ -C=O \end{matrix}$, $CH_2CH_2CO_2H$, or $=CHCHO$;

$R_3$ is methyl $\begin{pmatrix} -H \\ -CH_3 \end{pmatrix}$ or $\begin{pmatrix} -CH_3 \\ -OH \end{pmatrix}$;

$R_4$ is H, vinyl, ethyl, $-CHCH_3$,
                           |
                           OH $CH_2CH_2CO_2H$, $=CHCHO$; or $\begin{pmatrix} -H \\ -ethyl \end{pmatrix}$;

$R_5$ is methyl;
$R_6$ is H, $CH_2CH_2CO_2H$, $CH_2CH_2CO_2R$ or $CO_2H$ $R_7$ is $CH_2CH_2CO_2H$, $CH_2CH_2CO_2R$ or $\begin{pmatrix} -CH_2CH_2CO_2H \\ -H \end{pmatrix}$;

$R_8$ is methyl or $\begin{pmatrix} -CH_3 \\ -H \end{pmatrix}$ $R_9$ is H, COOH, $CH_2COOH$ or methyl;

provided that when $R_1$, $R_2$, $R_3$, $R_4$, $R_7$ and $R_8$ represent two substituents or are divalent and attached to the same carbon, the respective pyrrole ring to which attached is a dihydropyrrole;
R is lower alkyl or benzyl;
$R_6$ and $R_9$, taken together are

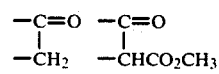

with the proviso that at least one of $R_1$–$R_9$ includes a free carboxyl group; and salts thereof.

These compounds are useful in the photodiagnosis and phototherapy of tumors.

42 Claims, No Drawings

OTHER PUBLICATIONS

*Current Microbiology,* 8, 195–199, 1983, by Gauthier, et al.
*Zhurnal Organicheshoi Kiii Mii,* 15, 828–835, 1979 by Bacunbee, et al.
Dougherty, et al., *Journal of the National Cancer Institute,* 55, 1976 pp. 115–119.
Wile, et al. "Laser Photoradiation Therapy of Recurrent Human Breast Cancer and Cancer of the Head and Neck," in *Porphyrin Photosensitization,* ed. by Kesser and Dougherty, Alan R. Liss, Inc., New York, N.Y., pp. 47–52 (1973).
Lin, et al., "HpD Photodetection of Bladder Carcinoma," in *Porphyrin Localization and Treatment of Tumors,* ed. by Doiron and Gomer, Alan R. Liss, Inc. New York, N.Y. pp. 187–199 (1984).
Aizawa, et al., "A New Diagnostic System for Malignant Tumors Using Hematoporphyrin Derivative, Laser Photoradiation and a Spectroscope," in *Porphyrin Localization and Treatment of Tumors,* ed. by Dorion and Gomer, Alan R. Liss, Inc., New York, N.Y., pp. 227–238 (1984).
Henderson, et al., "Studies on the Mechanism of Tumor Destruction by Photoradiation Therapy," in *Porphyrin Localization and Treatment of Tumors,* ed. by Dorion and Gomer, Alan R. Liss, Inc., New York, N.Y., pp. 601–612 (1984).
Hayata, et al., "Indications of Photoradiation Therapy in Early Stage Lung Cancer on the Basis of Post-PRT Histologic Findings," in *Porphyrin Localization and Treatment of Tumors,* ed. by Dorion and Gomer, Alan R. Liss, Inc., New York, N.Y., pp. 747–758 (1984).
Profio, et al., "Fluorescence of Hematoporphyrin-Derivative for Detection and Characterization of Tumors", in *Porphyrins in Tumor Photo-therapy,* ed. by Andreoni and Cubeddu, Plenum Press, New York, N.Y., pp. 321–337 (1984).
Benson, Ralph C., "The Use of Hematoporphyrin Derivative (HpD) in the Localization and Treatment of Transition Cell Carcinoma (TCC) of the Bladder," in *Porphyrin Localization and Treatment of Tumors,* ed. by Dorion and Gomer, Alan R. Liss, Inc., New York, N.Y., pp. 795–804 (1984).
Fioretti, et al., "Monitoring of Hematoporphyrin Injected in Humans and Clinical Prospects of Its Use in Gynecologic Oncology," in *Porphyrins in Tumor Phototherapy,* ed. by Andreoni and Cubeddu, Plenum Press, New York, N.Y., pp. 355–361 (1984).
Doiron, et al., "Hematoporphyrin Derivative Photoradiation Therapy of Endobronchial Lung Cancer," in *Porphyrins in Tumor Phototherapy,* ed. by Andreoni and Cubeddu, Plenum Press, New York, N.Y., pp. 395–403 (1984).
Spinelli, et al., "Endoscopic HpD-Laser Photoradiation Therapy (PRT) of Cancer," in *Porphyrins in Tumor Phototherapy,* ed. by Andreoni and Cubbeddu, Plenum Press, New York, N.Y., pp. 423–426 (1984).
Ohi, et al., "Photoradiation Therapy with Hematoporphyrin Derivative and an Argon Dye Laser of Bladder Carcinoma," in *Porphyrins in Tumor Phototherapy,* ed. by Andreoni and Cubbeddu, Plenum Press, New York, N.Y., pp. 439–446 (1984).
Bruce, R. A., Jr., "Photoradiation for Chorodial Malignant Melanoma," in *Porphyrins in Tumor Phototherapy,* ed. by Andreoni and Cubbeddu, Plenum Press, New York, N.Y., pp. 455–461 (1984).
Berenbaum, et al., "In Vivo Biological Activity of the Components of Haematoporphyrin Derivative", in *Br. J. Cander* pp. 571–581 (1982).

TETRAPYRROLE THERAPEUTIC AGENTS

FIELD OF THE INVENTION

This invention relates to new compounds which are useful in photodiagnosis and phototherapy, especially in the detection and treatment of tumors and cancerous tissues in the human or animal body.

DESCRIPTION OF THE PRIOR ART

It is known to irradiate tumors and cancerous tissues in the human body with intensive light following administration of a hematoporphyrin derivative in the wavelength range of 626 to 636 namometers to reduce and, at times, destroy the cancerous cells (see PCT published specification WO No. 83/00811). It is also known that porphyrins, especially the sodium salt of protoporphyrins, can maintain or promote the normal functions of cells and are useful for preventing the genesis, growth, metastasis , and relapse of malignant tumors, Japanese Published Patent Application No. 125757/76 describes the use of porphyrins as tumor inhibiting agents, exemplifying etioporphyrin, mesoporphyrin, protoporphyrin, deuteroporphyrin, hematoporphyrin, coprophyrin, and uroporphyrin.

In Tetrahedron Letters No. 23, pp. 2017-2020 (1978), there is described an amino monocarboxylic acid adduct of the pigment bonellin obtained by extraction of principally the body wall of the marine echuroid *B. viridis*. The structure of these adducts is presumed to be an amide formed through either of the free carboxy groups of bonellin and the amino monocarboxylic acid. Hydrolysis of the adduct yielded a mixture of valine, isoleucine, leucine and alloisoleucine. No use for these amino acid adducts is described in this reference.

That the tetrapyrroles cause intense photosensitivity in animals is well-known and has been documented in numerous articles in literature, e.g., J. Intr. Sci. Vitaminol, 27, 521-527 (1981); Agric. Biol. Chem., 46(9), 2183-2193 (1982); Chem. Abst. 98, 276 (1983) and 88, 69764m (1928).

SUMMARY OF THE INVENTION

The products contemplated by this invention are cyclic and acyclic tetrapyrroles derived by various procedures from naturally-occurring tetrapyrroles. The cyclic tetrapyrroles have as their common parent tetrapyrrole, uroporphyrinogen, and possess the following ring structure:

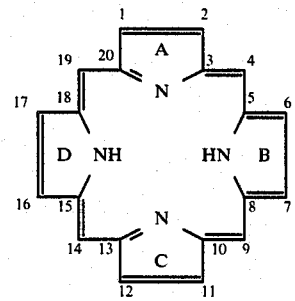

in which the positions in the molecule are numbered 1-20, and the rings identified by letters A, B, C and D, and also include perhydro-, e.g., dihydro- and tetrahydro-, derivatives of the said ring structure, e.g., compounds in which one or more double bonds are absent.

There are present in the ring system four pyrrole rings joined through the alpha positions of the respective pyrrole rings by a methine group, i.e., —CH=. The compounds of the present invention are designated as derivatives of the tetrapyrroles for convenience in the disclosure and the appended claims and it will be understood that the term "tetrapyrrole" will designate compounds of the characteristic ring structure designated hereinbefore as well as the corresponding perhydro derivatives, and the corresponding non-cyclic pyrroles, i.e., the linear tetrapyrroles, commonly known as the bile pigments.

The tetrapyrroles employed in the present invention are all derived by various means and various alteration procedures from natural tetrapyrroles. The naturally occurring tetrapyrroles have as their common ancestor uroporphyrinogen III, a hexahydroporphyrin reduced at the bridge positions. For example, synthetic or biosynthetic derivatives or products of protoporphyrins IX or protoporphyrinogen IX are well-known in the art (see, for example, Porphyrins and Metalloporphyrins, K. Smith Elsivier; The Porphyrins (Vols. 1-7) D. Dolphin, Academic Press; and Biosynthetic Pathways, Vol. III, Chapter by B. Burnham, editor D. M. Greenberg, Academic Press).

The non-cyclic tetrapyrroles are commonly known as bile pigments and include, for example, bilirubin and biliverdin. These tetrapyrroles are also derived from protoporphyrin, e.g., as metabolic products in animals.

A further characteristic of the present new compounds is the presence of at least one amide linkage in a substituent at any of the numbered positions of the ring structure. These are present in the instant new compounds together with other substituents as defined hereinafter.

Thus, the present invention contemplates amino acid or peptide derivatives of compounds which contain the chromophore of porphyrins, chlorins or bacteriochlorins, as well as related porphyrin compounds. The peptide linkage involves a carboxy group of the chromophore-bearing compound and the amino group of the specified amino acid. The present new compounds embrace, inter alia, derivatives of the tetrapyrroles which contain a free carboxy group. These derivatives include the major classes of tetrapyrroles: carboxy-containing porphyrins, chlorins, and bacteriochlorins, which are well-known to those skilled in this art.

The amino acid employed in the present invention to form the aforesaid peptide linkage are amino-dicarboxylic acids in which the amino group, of course, is located on a carbon atom of the dicarboxylic acid. The specific position of the amino group in the carbon atom chain is not critical, the only requirement being that the amino group be available to form the requisite peptide linkage with the carboxyl group of the selected porphyrin. Thus, a variety of amino dicarboxylic acids are useful in the present invention, including α-aminosuccinic (aspartic), α-aminoglutaric (glutamic), beta-aminoglutaric, betaaminosebacic, 2,6-piperidinedicarboxylic, 2,5-pyrroledicarboxylic, 2-carboxypyrrole-5-acetic, 2-carboxypiperidine-6-propionic, α-aminoadipic,α-aminoazelaic, and similar such acids. These amino acids may be substituted with angular alkyl groups such as methyl and ethyl groups, as well as other groups which do not adversely affect the capability of the amino group to form the peptide linkage, e.g., alkoxy groups or acyloxy groups, and may also include additional amino groups. The preferred amino acids are the naturally occurring α-amino acids, glutamic and aspartic acids, whch are readily available and, up to the present, have provided the best results.

Exemplary compounds of the tetrapyrrole classes are illustrated in Table I in which the numbered positions of the tetrapyrrole ring structure are used to designate the position of the indicated substituent. The absence of double bonds in the ring system is designated under "dihydro" with each set of numbers (ring position) indicating the absence of a double bond between the designated positions.

TABLE I

| PORPHYRIN | A 1 | A 2 | B 6 | B 7 | C 11 | C 12 | C 14 | D 16 | D 17 | Dihydro |
|---|---|---|---|---|---|---|---|---|---|---|
| Coproporphyrin III | Me | Pr | Me | Pr | Me | Pr | H | Pr | Me | — |
| Deuteroporphyrin IX | Me | H | Me | H | Me | Pr | H | Pr | Me | — |
| Hematoporphyrin IX | Me | Me−CH−OH | Me | Me−CH−OH | Me | Pr | H | Pr | Me | — |
| Protoporphyrin IX | Me | V | Me | V | Me | Pr | H | Pr | Me | — |
| Photoprotoporphyrin IX | Me | V | {−Me, −OH} | =CHCHO | Me | Pr | H | Pr | Me | 6,7 |
| Mesoporphryin IX | Me | Et | Me | Et | Me | Pr | H | Pr | Me | — |
| Pyropheophorbide $\underline{a}$ | Me | V | Me | Et | Me | C(=O)−CH$_2$ | | {Pr, H} | {Me, H} | 16,17 |
| Transmesochlorin IX | {H, Me} | {H, Et} | Me | Et | Me | Pr | H | Pr | Me | 1,2 |
| Transmesochlorin IX | Me | Et | {H, Me} | {H, Et} | Me | Pr | H | Pr | Me | 6,7 |
| Pheophorbide $\underline{a}$ | Me | V | Me | Et | Me | C(=O)−CH(CO$_2$Me) | | {Pr, H} | {Me, H} | 16,17 |
| Chlorin e$_4$ | Me | V | Me | Et | Me | CO$_2$H | Me | {H, Pr} | {H, Me} | 16,17 |
| Chlorin e$_6$ | Me | V | Me | Et | Me | CO$_2$H | Ac | {H, Pr} | {H, Me} | 16,17 |
| Mesochlorin e$_4$ | Me | Et | Me | Et | Me | CO$_2$H | Me | {H, Pr} | {H, Me} | 16,17 |
| Isochlorin e$_4$ | Me | V | Me | Et | Me | H | Ac | {H, Pr} | {H, Me} | 16,17 |
| Mesoisochlorin e$_4$ | Me | Et | Me | Et | Me | H | Ac | {H, Pr} | {H, Me} | 16,17 |
| Mesochlorin e$_6$ | Me | Et | Me | Et | Me | CO$_2$H | Ac | {H, Pr} | {H, Me} | 16,17 |
| Bacteriopheophorbide $\underline{a}$ | Me | ACL | {H, Me} | {H, Et} | Me | C(=O)−CH(CO$_2$Me) | | {H, Pr} | {H, Me} | 6,7 16,17 |

TABLE I-continued

| PORPHYRIN | Ring Position | | | | | | | | |
|---|---|---|---|---|---|---|---|---|---|
| | A | | B | | C | | | D | |
| | 1 | 2 | 6 | 7 | 11 | 12 | 14 | 16 | 17 | Dihydro |
| Pyrobacteriopheophorbide a | Me | ACL | {H, Me} | {H, Et} | Me | C=O—CH$_2$ | | {H, Pr} | {H, Me} | 6,7 16,17 |
| Bacteriochlorin e$_6$ | Me | ACL | {H, Me} | {H, Et} | Me | CO$_2$H | Ac | {H, Pr} | {H, Me} | 6,7 16,17 |
| Bacteriochlorin e$_4$ | Me | ACL | {H, Me} | {H, Et} | Me | CO$_2$H | Me | {H, Pr} | {H, Me} | 6,7 16,17 |
| Bacterioisochlorin e$_4$ | Me | ACL | {H, Me} | {H, Et} | Me | H | Ac | {H, Pr} | {H, Me} | 6,7 16,17 |

Notes:
Me: —CH$_3$ (Methyl group)
Pr: —CH$_2$CH$_2$COOH (Propionic acid group)
V: —CH=CH$_2$ (Vinyl group)
Et: —CH$_2$CH$_3$ (Ethyl group)
Ac: —CH$_2$COOH (Acetic acid group)
ACL: CH$_3$—CO— (Acetyl group)

The present new compounds are mono- or polyamides of an aminodicarboxylic and a tetrapyrrole containing at least one carboxyl group of the structure

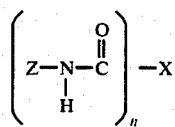

wherein Z is the aminodicarboxylic acid residue less the amino group and X is the tetrapyrrole residue less the carboxy group and "n" is an integer from 1 to 4 inclusive.

The particularly preferred compounds are fluorescent mono- or polyamides of an aminodicarboxylic acid and a tetrapyrrole compound of the formula:

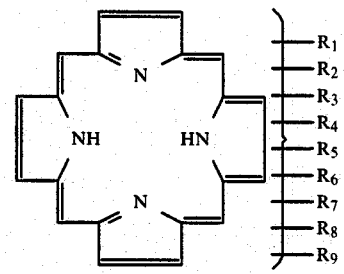

or the corresponding di- or tetrahydrotetrapyrroles wherein $R_1$ is methyl; $\begin{cases} -H \\ -CH_3 \end{cases}$ or $\begin{cases} -OH \\ -CH_3 \end{cases}$;

$R_2$ is H, vinyl, ethyl, —CHCH$_3$(OH), acetyl, $\begin{cases} -H \\ -ethyl \end{cases}$, —C=O, CH$_2$CH$_2$CO$_2$H, or =CHCHO;

$R_3$ is methyl $\begin{cases} -H \\ -CH_3 \end{cases}$ or $\begin{cases} -CH_3 \\ -OH \end{cases}$;

$R_4$ is H, vinyl, ethyl, —CHCH$_3$(OH),

CH$_2$CH$_2$CO$_2$H, =CHCHO; or $\begin{cases} -H \\ -ethyl \end{cases}$;

$R_5$ is methyl;
$R_6$ is H, CH$_2$CH$_2$CO$_2$H, CH$_2$CH$_2$CO$_2$R or CO$_2$H;

$R_7$ is CH$_2$CH$_2$CO$_2$H, CH$_2$CH$_2$CO$_2$R, or $\begin{cases} -CH_2CH_2CO_2H \\ -H \end{cases}$;

$R_8$ is methyl or $\begin{cases} -CH_3 \\ -H \end{cases}$ $R_9$ is H, COOH, CH$_2$COOH or methyl;

provided that when $R_1$, $R_2$, $R_3$, $R_4$, $R^7$ and $R^8$ represent two substituents or are divalent and attached to the same carbon, the respective pyrrole ring to which attached is a dihydropyrrole;
R is lower alkyl or benzyl;
$R_6$ and $R_9$, taken together are —C=O or —C=O
|            |
—CH$_2$    —CHCO$_2$CH$_3$ with the proviso that at least one of $R_1$–$R_9$ includes a free carboxyl group; and salts thereof.

The especially preferred amides of the invention are derived from tetrapyrroles of the formula:

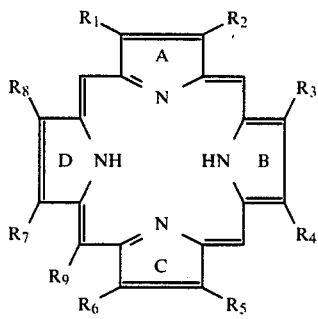

or the corresponding di- or tetrahydrotetrapyrroles and salts thereof, wherein $R_1-R_9$ are as previously defined.

Particularly preferred compounds of this invention include:

Chlorin Derivatives

Mono and diaspartyl trans-mesochlorin IX
Mono and diglutamyl trans-mesochlorin IX
Mono, di and triaspartyl chlorin $e_6$
Mono, di and triaspartyl mesochlorin $e_6$
Mono, di and triglutamyl chlorin $e_6$
Mono, di and triglutamyl mesochlorin $e_6$
Mono and diaspartyl chlorin $e_4$
Mono and diaspartyl mesochlorin $e_4$
Mono and diaspartyl isochlorin $e_4$
Mono and diaspartyl mesochlorin $e_4$
Mono and diglutamyl chlorin $e_4$
Mono and diglutamyl mesochlorin $e_4$
Mono and diglutamyl isochlorin $e_4$
Mono and diglutamyl mesoisochlorin $e_4$
Monoaspartylpyropheophorbide a
Monoglutamylpyropheophorbide a
Monoaspartylpheophorbide a
Monoglutamylpheophorbide a
Mono and diaspartylphotoprotoporphyrin IX
Mono and diglutamylphotoprotoporphyrin IX
Mono and di-L-alpha-aminoadipyl trans-mesochlorin IX

Porphyrins Derivatives

Mono and diaspartylmesoporphyrin IX
Mono and diglutamylmesoporphyrin IX
Mono and diaspartylprotoporphyrin IX
Mono and diglutamyl protoporphyrin IX
Mono and diaspartyldeuteroporphyrin IX
Mono and diglutamyldeuteroporphyrin IX
Mono, di, tri and tetraaspartylcoproporphyrin III (isomer mixture)
Mono, di, tri and tetraglutamylcoproporphyrin III
Mono and diaspartylhematoporphyrin IX
Mono and diglutamylhematoporphyin IX

Bacteriochlorin Derivatives

Mono and diaspartylbacteriochlorin $e_4$
Mono and diglutamylbacteriochlorin $e_4$
Mono and diaspartylbacterioisochlorin $e_4$
Mono and diglutamylbacterioisochlorin $e_4$
Mono, di and triaspartylbacteriochlorin $e_6$
Mono, di and triglutamylbacteriochlorin $e_6$
Monoaspartylpyrobacteriopheophorbide a
Monoglutamylpyrobacteriopheophorbide a
Monoaspartylbacteriopheophorbide a
Monoglutamylbacteriopheophorbide a The present new compounds form salts with either acids or bases. The acid salts are particularly useful for purification and/or separation of the final amide products as are the salts formed with bases. The base salts, however, are particularly preferred for diagnostic and therapeutic use as hereindescribed.

The acid salts are formed with a variety of acids such as the mineral acids, hydrochloric, hydrobromic, nitric and sulfuric acids, organic acids such as toluenesulfonic and benzenesulfonic acids.

The base salts include, for example, sodium, potassium, calcium, magnesium, ammonium, triethylammonium, trimethylammonium, morpholine and piperidine salts and similar such salts.

The acid and base salts are formed by the simple expediency of dissolving the selected amino acid tetrapyrrole amide in an aqueous solution of the acid or base and evaporation of the solution to dryness. The use of a water-miscible solvent for the amide can assist in dissolving the amide.

The final amide products can also be converted to metal complexes for example by reaction with metal salts. The magnesium complexes may be useful for the same purpose as the adduct product. Other metal complexes, as well as the magnesium complex, including, for example, iron and zinc, are useful to preclude contamination during processing of the adduct product by metals such as nickel, cobalt and copper, which are difficult to remove. Zinc and magnesium are readily removed from the final adduct product after processing is completed.

Since many of the aminodicarboxylic acids exist in both the D- and L-forms, and also are employed in mixtures of these forms as well as the D,L-form, the selection of the starting amino acid will, of course, result in products in which the respective isomer or mixture of isomers exist. The present invention contemplates the use of all such isomers, but the L-form is particularly preferred.

The present new compounds are prepared by the usual peptide synthetic routes which generally include any amide-forming reaction between the selected amino acid and the specific tetrapyrrole. Thus, any amide-forming derivative of the tetrapyrrole carboxylic acid can be employed in producing the present new peptides, e.g., lower alkyl esters, anhydrides and mixed anhydrides.

The preferred preparative methods use mixed anhydrides of the carboxylic acid or carbodiimides. The reactants are merely contacted in a suitable solvent therefor and allowed to react. Temperatures up to the reflux temperature can be used, with the higher temperatures merely reducing the reaction time. Excessively high temperatures are usually not preferred so as to avoid unwanted secondary reactions however.

The procedures for forming the instant peptides are well known in this art and are provided in detail in the accompanying examples.

When the selected tetrapyrrole contains more than one carboxyl group, then mixtures of products can be formed including isomeric monopeptide products and di- and even tri- or higher peptide products, depending on the number of carboxyl groups and depending on the selected stoichiometry. Thus, when equimolar mixtures of amino acid and tetrapyrrole are reacted, not only monopeptides but also dipeptides are obtained, although the monopeptide would predominate. With higher molar ratios, the nature of the products will similarly vary. It is generally possible to separate the monopeptides and higher peptides using known chromatographic techniques. However, such separations are not necessary since the mixed peptides are usually comparable to the separated products in their ultimate use. Thus, mixtures of the mono-, di- and tri-peptides of the same tetrapyrrole can be used.

Usually, unreacted tetrapyrrole is separated from the peptide products of the invention during purification as, for example, by chromatographic techniques.

Photodiagnosis and Phototherapy

The compounds of the present invention are useful for the photodiagnosis and phototherapy of tumor, cancer and malignant tissue (hereinafter referred to as "tumor").

When a man or animal having tumor is treated with doses of a compound of the present invention and when appropriate light rays or electromagnetic waves are applied, the compound emits light, i.e., fluorescence. Thereby the existence, position and size of tumor can be detected, i.e., photodiagnosis.

When the tumor is irradiated with light of proper wavelength and intensity, the compound is activated to exert a cell killing effect against the tumor. This is called "phototherapy".

Compounds intended for photodiagnosis and phototherapy ideally should have the following properties:
(a) non-toxic at normal therapeutic dosage unless and until activated by light;
(b) should be selectively photoactive;
(c) when light rays or electromagnetic waves are applied, they should emit characteristic and detectable fluorescence;
(d) when irradiated with light rays or electromagnetic waves are applied, they are activated to an extent to exert a cell killing effect against tumor; and
(e) easily metabolized or excreted after treatment.

In accordance with testing up to the present, the present new compounds have the foregoing properties and are also characterized by reasonable solubility in water at physiological pH.

The present new compounds possess greater fluorescence in tumors than do the corresponding basic tetrapyrroles, and even peptides formed with amino monocarboxylic acids, e.g., alanine and epsilon aminocaproic acid. Their use provides the best contrast in tumors compared to normal tissue around the tumor. The instant compounds absorb activating energy for phototherapy in the convenient range of 600 to 800 nanometers, with the preferred compounds absorbing in the 620-760 nanometer range, i.e., light of longer wavelengths which more readily permits penetration of energy into the tumor for phototherapeutic purpose.

In present experience, the present compounds more uniformly distribute throughout the tumor than the basic tetrapyrrole permitting the use of considerably lower dosage (to about 1/10th of the required normal dose of the basic tetrapyrrole) which lessens, if not eliminates, photosensitization in the host. They also possess a more consistent fluorescence whereas some of the corresponding tetrapyrroles show inconsistent fluorescence or the fluorescence varies from day to day in the host.

A particularly advantageous property of the present compounds resides in the ease with which they are excreted by the host. Generally, within 24 to 72 hours of intravenous or intraperitonal administration, there are little or no detectable amounts in normal muscle tissue. Up to about 50% of the present compounds are recovered from the feces of the host within 24-72 hours of injection whereas under equivalent circumstances, substantial amounts of the corresponding tetrapyrroles remain, and up to about 20% of peptides formed with amino monocarboxylic acids remain. This property is extremely important in that it contributes to minimization of photosensitization of the host.

The instant compounds can be used for diagnosis and therapeutic treatment of a broad range of tumors. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkins's disease, multiple myeloma, renal cancer, leukemia, and malignant lymphocytoma. For diagnosis, the sole requirement is that the tumor be capable of selectively fluorescing when exposed to proper light. For treatment, the tumor must be penetrable by the activation energy. For diagnosis, light of shorter wavelength is used whereas for therapeutic purposes light of longer wavelength is used to permit ready penetration of the tumor tissue. Thus, for diagnosis, light of from 360-420 nanometers can be used, and for treatment, from 620 to 760, depending on the individual characteristics of the tetrapyrrole. The absorption characteristics of the present new compounds are substantially the same as the tetrapyrrole from which derived.

It is necessary that the light rays be so intense as to cause the compounds to emit fluorescence for diagnosis and to exert a cell killing effect for therapy.

The source of irradiation for photodiagnosis and phototherapy is not restricted, however, but the laser beam is preferable because intensive light rays in a desired wavelength range can be selectively applied. For example, in photodiagnosis, the compound of the invention is administered to a human or animal body, and after a certain period of time, light rays are applied to the part to be examined. When an endoscope can be used for the affected part, such as lungs, gullet, stomach, womb, urinary bladder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser beams from the tip of quartz fibers. Besides the irradiation of the surface of tumor, the internal part of the tumor can be irradiated by inserting the tip of quartz fibers into the tumor. The irradiation can be visually observed or imaged on a CRT screen.

For photodiagnosis, light of wavelengths between 360 and 420 nm. is suitable for activating the present tetrapyrrole compounds. Of course, each compound has a specific optimal wavelength of activation. A long wavelength ultraviolet lamp is particularly suitable for photodiagnosis. Similar methods for viewing of the treated tumor can be used as already described for phototherapy.

The dosages of the present new compounds will vary depending on the desired effect, whether for diagnosis or for treatment. For diagnosis, doses of as little as 1 mg/kg will be effective, and up to about 7.5 mg/kg can be used. For treatment, the dose will usually approximate about 0.5 mg/kg. Of course, the dosage for either diagnosis or treatment can be varied widely in view of aforesaid advantageous properties of the present compounds, e.g., the ease of elimination from the host, for one.

The present compounds are apparently nontoxic at the dosage levels employed for diagnosis or treatment. No mortality of test animals due the present compounds has been noted in studies employing dosage levels up to 14 mg/kg.

For both diagnosis and treatment, the present compounds can be administered by the oral, intravenous, or intramuscular routes. They can be formulated as lyophilized sterile, pyrogen-free compounds, preferably in the form of basic salts, e.g., sodium salt. The preferred dosage forms are provided as injectable solutions (isotonic).

The irradiation source used in treatment of tumors containing compounds of this invention is a filtered, high-intensity, continuous source or pumped dye, or other laser and light delivery system, which is capable of performing within the following limits: power intensity 20–500 mw/cm$^2$ at wavelengths between 620 and 680 nm. and a total output of at least 4 watts or greater. Several currently commercially available lasers meet these criteria.

The tetrapyrroles can be prepared by various synthetic methods which are found in the literature, e.g., Pheophorbides
 Willstatter, R., Stoll, A.; *Investigations on Chlorophyll*, (Transl. Schertz, FM. M., Merz, A. R.) p. 249. Science Printing Press, Lancaster, Pa., 1928.
 Pennington, F. C., Strain, H. H., Svec, W. A., Katz, J. J.; *J. Amer. Chem. Soc.*, 86, 1418 (1964).

Chlorin $e_6$
 Willstatter, R., Stoll, A.; *Investigations on Chlorophyll*, (Trans., Schertz, F. M., Merz, A. R.,) p. 176. Science Printing Press, Lancaster, Pa., 1928.
 Willstatter, R., Isler, M.; *Ann. Chem.*, 390, 269 (1912).
 Fisher, H., Baumler, R.; *Ann. Chem.*, 474, 65 (1929).
 Fisher, H., Siebel, H.; *Ann. Chem.*, 499, 84 (1932).
 Conant, J. B., Mayer, W. W.; *J. Amer. Chem. Soc.*, 52, 3013 (1930).

Chlorin $e_4$
 Fisher, H., Heckmaier, J., Plotz, E.; *Justus Leibigs Ann. Chem.*, 500 215 (1933).

Chlorin $e_6$, $e_4$, isochlorin $e_4$, mesochlorin $e_6$, bacteriopheophorbide, bacteriochlorin $e_6$
 Fischer and Orth, "Des Chemie des Pyrrole" Akademische Verlazsgesellschaft, Leipzig, 1940, Vol. II, Part 2.

General Reference for Porphyrins
 "Porphyrins and Metalloporphyrins" ed. Kevin M. Smith, Elsevier 1975 N.Y.

The compounds of the present invention can be administered to the host in a variety of forms adapted to the chosen route of administration, i.e., orally, intraveneously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present new compounds may also be applied directly to tumors, whether internal or external, in the host in topical compositions. Exemplary compositions include solutions of the new compounds in solvents, particularly aqueous solvents, most preferably water. Alternatively, for topical application particularly to skin tumors, the present new compounds may be dispersed in the usual cream or salve formulations commonly used for this purpose or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

EXAMPLE 1

Di (D,L) aspartyl transmesochlorin IX (Carbodiimide Method)

140 mg of transmesochlorin and 200 mg of (D,L) aspartic acid dimethyl ester hydrochloride were dissolved in 30 ml of dimethyl formamide. 300 mg of N,N'-dicyclohexyl-carbodiimide was added. The reaction was allowed to stand for one hour, then another 300 mg of carbodiimide was added. This procedure was repeated twice and then the reaction mixture was allowed to stand overnight. The reaction may be monitored by thin layer chromatography on silica, using solvent benzene/methanol/88% formic acid 8.5/1.5/0.13 V/V/V.

The disubstituted chlorin has the highest $R_f$ value, the unsubstituted chlorin has the lowest, with the monosubstituted isomers in between and unresolved.

After standing overnight, the reaction mixture appeared to contain at least 50% of the disubstituted chlorin. The solvent was removed under vacuum and the remaining solid dissolved in 50 ml of 3N HCl.

The solution was allowed to stand at room temperature for 48 hours to hydrolyze the ester groups, then the chlorin mixture was precipitated at pH 2.5-3 and collected and washed with water at the centrifuge.

The chlorin mixture was purified by dissolving in 0.05M $NH_4OH$ and applying to a reverse phase (C-18 silica)column 2.5 cm $\times$ 30 cm. The elution procedure is a linear gradient from 40 to 70% methanol in 0.01M $KPO_4$ buffer pH 6.85 (1 liter total volume).

The leading green band (di D, L aspartyl transmesochlorin IX) was collected and flash evaporated to remove the methyl alcohol, the solution then precipitated at pH 2.5-3 and collected and washed 3 times at the centrifuge with dilute acetic acid. The product was dried under vacuum. The yield was 67 mg of di (D,L) aspartyl transmesochlorin IX.

EXAMPLE 2

Di and Mono (L) glutamyl transmesochlorin IX (mixed anhydride method)

50 mg (0.000087 moles) of transmesochlorin IX was dissolved in 100 ml of tetrahydrofuran (THF). 210 $\mu$l (0.002 moles) of triethylamine was added with stirring. After 10 minutes, 195 $\mu$l (0.00179 moles) of ethylchloroformate was added. After stirring 10 minutes, 50 ml (0.01 moles) of 0.2M KOH containing 250 mg (0.00169 moles) of (L) glutamic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5 $\times$ 30 cm. The reaction mixture was resolved using a linear gradient of 40-80% methanol in 0.01M $KPO_4$ buffer pH 6.85 (1 liter total volume).

The column effluent was collected via fraction collector and the tube contents were pooled according to individual components. The order of elution was di (L) glutamyl transmesochlorin IX, mono (L) glutamyl transmesochlorin IX, and unsubstituted transmesochlorin IX.

The methanol was flashed off and the material was precipitated at pH 2.5-3.0. The ppt was washed 3 times with dilute acetic acid in water. The product was dried under vacuum.

EXAMPLE 3

Di and mono (D,L) aspartyl photoprotoporphyin IX (mixed anhydride method)

313.4 mg of photoprotoporphyrin IX (isomer mixture) was dissolved in 100 mls of tetrahydrofuran (THF). 210 μl of triethylamine was added with stirring. After 10 minutes, 210 μl of ethyl chloroformate was added. After stirring for 10 minutes, 50 mls of 0.2 m KOH, containing 450 mgs of (D,L) aspartic acid, were added to the THF solution. This mixture was stirred for one hour at room temperature.

The organic solvent was flashed off and the reaction mixture was checked by silica TLC. Benzene/methanol/88% formic acid (8.5/1.5/0.13) was used to develop the chromatogram.

After checking for product, the pH of the mixture was adjusted to 7.5–8.0 and the solution was placed on a reverse phase (C-18 silica) column 2.5×30 cm. The reaction mixture was resolved using a linear gradient of 40/80% MeOH in 0.01M $KPO_4$ buffer pH 6.85 (1 liter total volume).

The column effluent was collected via a fraction collector and the tube contents were pooled according to individual components.

The methanol was flashed off and the material was precipitated at pH 3.0–3.5. The ppt was washed 3 times with dilute acetic acid in $H_2O$. The product was dried under vacuum. The yield of mono(D,L) aspartyl photoprotoporphyrin IX was 54 mg. The yield of di (D,L) aspartyl photoprotoporphyrin IX was 227.8 mg.

EXAMPLE 4

Di and Mono (L) aspartyl protoporphyrin IX (mixed anhydride method)

100 mg of protoporphyrin IX was dissolved in 100 ml of P-dioxane. 210 μl of triethylamine was added. After stirring 10 minutes, 50 μl of 0.2M KOH containing 500 mg of (L) aspartic acid was added to the dioxane solution. This mixture was stirred for one hour at room temperature.

The organic solvent was flashed off and the reaction mixture was checked by silica TLC for product. Benzene/methanol/88% formic acid (8.5/1.5/0.13) was used to develop the chromatogram.

After checking for product, the pH of the solution was adjusted to pH 7.5–8.0 and placed on a reverse phase (C-18 silica) column 2.5×30 cm. The reaction mixture was resolved using a linear gradient of 40–70% methanol in 0.01M $KPO_4$ buffer pH 6.85 (1 liter total volume).

The column effluent was collected via a fraction collector and the tube contents were pooled according to individual components.

The methanol was flashed off and the material was precipitated at pH 2.5–3.0. The ppt was washed 3 times with dilute acetic acid in $H_2O$. The product was then dried under vacuum. The yield of mon (L) aspartyl protoporphyrin IX was 12.3 mg and di (L) aspartyl protoporphyrin IX was 54 mg.

EXAMPLE 5

Di and mono (L) aspartyl mesoporphyrin IX (mixed anhydride method)

200 mg of mesoporphyrin IX was dissolved in 100 ml of tetrahydrofuran (THF). 210 μl of triethylamine was added to the THF solution. After 10 minutes of stirring 210 μl ethyl chloroformate was added and stirred 10 minutes. 50 ml of 0.2M KOH containing 500 mg of (L) aspartic acid was added to the THF solution and allowed to stir one hour at room temperature.

The organic solvent was flashed off and the reaction mixture was checked for product by silica TLC using benzene/methanol/88% formic acid (8.5/1.5/0.13) to develop the chromatogram.

After checking for product, the pH of the mixture was adjusted to 7.5–8.0 and placed on a reverse phase (C-18 silica) column 2.5×30 cm. The reaction mixture was resolved using a linear gradient of 40–80% methanol in 0.01M $KPO_4$ buffer pH 6.85 (1 liter total volume).

The column effluent was collected via fraction collector and the tube contents were pooled according to individual components.

The methanol was flashed off and the material was precipitated at pH 3.0–3.5. The ppt was washed 3 times with dilute acetic acid in $H_2O$. The product was dried under vacuum with a yield of 41.5 mg mono (L) aspartyl mesoporphyrin and 175.1 mg di (L) aspartyl mesoporphyrin.

EXAMPLE 6

Di and Mono (L) aspartyl deuteroporphyrin IX (mixed anhydride method)

100 mg deuteroporphyrin IX was dissolved in 50 ml of p-dioxane. 210 μl of triethylamine was added with stirring. After 10 minutes, 210 μl of isobutyl chloroformate was added. After stirring 10 minutes, 50 ml of 0.2 M KOH containing 500 mg of L aspartic acid was added to the dioxane solution. This mixture was stirred for one hour at room temperature.

The organic solvent was flashed off and the reaction mixture was checked by silica TLC Benzene/ methanol/88% formic acid (8.5/1.5/0.13) was used to develop the chromatogram.

After checking for product, the pH of the mixture was adjusted to 7.5–8.0 and placed on a reverse phase (C-18 silica) column 2.5×30 cm. The reaction mixture was resolved using a linear gradient of 40–70% methanol in 0.01 M $KPO_4$ buffer pH 6.85 (1 liter total volume).

The column effluent was collected via fraction collector and the tube contents were pooled according to individual components.

The MeOH was flashed off and the material was precipitated at pH 2.5–3.0. The ppt was washed 3 times with dilute acetic acid in $H_2O$. The product was then dried under vacuum. The yield of mono (L) aspartyl deuteroporphyrin IX was 10 mg.

EXAMPLE 7

(L) Aspartyl pyropheophorbide a (mixed anhydride method)

80 mg of pyropheophorbide a was dissolved in 100 ml of tetrahydrofuran (THF) 210 μl of triethylamine was to the THF solution. After 10 minutes of stirring, 210 μl of ethylchloroformate was added and stirred 10 minutes. 50 ml of 0.2 M KOH containing 500 mg of (L) aspartic acid was added to the THF solution and allowed to stir one hour at room temperature.

The organic solvent was flashed off and the reaction mixture was checked for product by silica TLC using benzene (methanol) 88% formic acid (8.5/1.5/0.13) to develop the chromatogram.

After checking for product, the pH of the mixture was adjusted to 7.5–8.0 and placed on a reverse phase (C-18 silica) column 2.5×30 cm. The reaction mixture was resolved using a linear gradient of 40–80% methanol in 0.01 M KOH buffer pH 6.85 (1 liter total volume).

The column effluent was collected via fraction collector and the tube contents were pooled according to individual components.

The methanol was flashed off and the material was precipitated at pH 3.0–3.5. The ppt was washed 3 times with dilute acetic acid in H20. The product was dried under vacuum to produce a yield of 62 mg (L) aspartyl pyropheophorbide a.

EXAMPLE 8

Tetra, tri, and di (D,L) aspartyl coproporphyrin III (mixed anydride method)

150 mg of coproporphyrin III was dissolved in 100 ml of tetrahydrofuran (THF). 210 μl of triethylamine was added and stirring was continued at 20° C. for ten minutes. 210 μl of ethylchloroformate was next added and stirred for ten minutes.

50 ml of 0.2 M KOH containing 250 mg of (D,L) aspartic acid was added to the THF solution. This mixture was then stirred for one hour.

The organic solvent was flashed off and the reaction mixture was checked by silica TLC using the following solvent system: (benzene/methanol/88% formic acid (8.5/4.0/0.2).

The pH of this mixture was then adjusted to 7.5–8.0 and chromatographed on a reverse phase (C-18 silica) 2.5×30 cm column. The reaction mixture was resolved using 5–50% methanol in 0.01 in $KPO_4$ buffer pH 6.85 (1 liter total volume).

The column effluent was collected via a fraction collector and the tube contents were pooled according to individual components. The methanol was flashed off and the material was precipitated at pH 3.0–3.5. The ppt was washed 3 times with dilute acetic acid in water. The products were dried under vacuum and the yields were as follows: Tetra (D,L) aspartyl coproporphyrin III 94 mg, Tri (D,L) aspartyl coproporphyrin III 77.2 mg, Di (D,L) aspartyl coproporphyrin III, 28.4 mg.

EXAMPLE 9

Di and mono (DL) aspartyl deuteroporphyrin IX (mixed anhydride method)

175 mg (0.00195 moles) of deuteroporphyrin IX was dissolved in 200 ml of tetrahydrofuran (THF). 210 ul (0.002 moles) of triethylamine was added with stirring. After 10 minutes, 210 ul (0.0019 moles) of ethylchloroformate was added. After stirring 10 minutes, 50 ml (0.01 moles) of 0.2 M KOH containing 200 mg (0.003 moles) of (DL) aspartic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/01.3) was used to develop the chromatogram.

After checking for product, the solution was adjusted to pH 7.5–8.0 and placed on a reverse phase (C-18 silica) column 2.5×30 cm. The reaction mixture was resolved using a linear gradient of 40–65% methanol in 0.01 M $KPO_4$ buffer pH 6.85 (1 liter total volume).

The column effluent was collected via fraction collector and the tube contents were pooled according to individual components. The order of elution was di (DL) aspartyl deuteroporphyrin IX, mono (DL) aspartyl deuteroporphyrin IX, and unsubstituted deuteroporphyrin IX.

The methanol was flashed off and the material was precipitated at pH 2.5–3.0. The ppt was washed 3 times with dilute acetic acid in water. The product was dried under vacuum.

EXAMPLE 10

Di and mono (DL) aspartyl hematoporphyrin IX (mixed anhydride method)

400 mg (0.0059 moles) of hematoporphyrin IX was dissolved in 50 ml of tetrahydrofuran (THF). 360 μl (0.0034 moles) of triethylamine was added with stirring. After 10 minutes, 340 μl (0.0031 moles) of ethylchloroformate was added. After stirring 10 minutes, 10 ml (0.01 moles) of 1 M KOH containing 600 mg (0.0045 moles) of (DL) aspartic acid was added to the THF solution. This mixture was stirred 90 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5–8.0 and placed on a reverse phase (C-18 silica) column 2.5×30 cm. The reaction mixture was resolved using a linear gradient of 20–70% methanol in 0.01 M $KPO_4$ buffer pH 6.85 (1 liter total volume).

The column effluent was collected via fraction collector and the tube contents were pooled according to individual components. The order of elution was di (DL) aspartyl hematoporphyrin IX, mono(DL) aspartyl hematoporphyrin IX, and unsubstituted hematoporphyrin IX.

The methanol was flashed off and the material was precipitated at pH 2.5–3.0. The ppt was washed 3 times with dilute acetic acid in water. The product was dried under vacuum.

EXAMPLE 11

Di and mono (D,L) aspartyl protoporphyrin IX (mixed anhydride method)

300 mg (0.00053 moles) of protoporphyrin XI was dissolved in 100 ml of tetrahydrofuran (THF). 210 μl (0.002 moles) of triethylamine was added with stirring. After 10 minutes, 210 μl (0.0019 moles) of ethylchloroformate was added. After stirring 10 minutes, 50 ml (0.01 moles) of 0.2M KOH containing 450 mg (0.0033 moles) of (D,L) aspartic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5–8.0 and placed on a reverse phase (C-18 silica) column 2.5×30 cm. The reaction mixture was resolved using a linear gradient of 40–65% methanol in 0.01M $KPO_4$ buffer pH 6.85 (1 liter total volume).

The column effluent was collected via a fraction collector and the tube contents were pooled according to individual components. The order of elution was di (D,L) aspartyl protoporphyrin IX, mono (D,L) aspartyl protoporphyrin IX, and unsubstituted protoporphyrin IX.

The methanol was flashed off and the material was precipitated at pH 2.5–3.0. The ppt was washed 3 times with dilute acetic acid in water. The product was dried under vacuum.

EXAMPLE 12

Mono (DL) aspartyl pyropheophorbide a (mixed anhydride method)

100 mg (0.000187 moles) of pyropheophorbide a was dissolved in 100 ml of tetrahydrofuran (THF). 210 μl (0.002 moles) of triethylamine was added with stirring. After 10 miniutes, 210 μl (0.0019 moles) of ethylchloroformate was added. After stirring 10 minutes, 50 ml (0.01 moles) of 0.2 M KOH containing 200 mg (0.0015 moles) of (DL) aspartic acid was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 40-80% methanol in 0.01 M KPO$_4$ buffer pH 6.85 (1 liter total volume).

The column effluent was collected via fraction collector and the tube contents were pooled according to individual components. The order of elution was mono (DL) aspartyl pyropheophorbide a, and then unsubstituted pyropheophorbide.

The methanol was flashed off and the material was precipitated at pH 2.5-3.0. The ppt was washed 3 times with dilute acetic acid in water. The product was dried under vacuum.

EXAMPLE 13

Di and mono L-alpha-aminoadipyl transmesochlorin IX (mixed anhydride method)

500 mg (0.000087 moles) of transmesochlorin IX was dissolved in 100 ml of tetrahydrofuran (THF). 210 μl (0.002 moles) of triethylamine was added with stirring. After 10 minutes, 210 μl (0.0019 moles) of ethylchloroformate was added. After stirring 10 minutes, 50 ml (0.01 moles) of 0.2 M KOH containing 250 mg (0.00155 moles) of L-alpha-aminoadipic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 40-80% methanol in 0.01 M KPO$_4$ buffer pH 6.85 (1 liter total volume).

The column effluent was collected via fraction collector and the tube contents were pooled according to individual components. The order of elution was di L-alpha-aminoadipyl transmesochlorin IX, and unsubstituted transmesochlorin IX.

The methanol was flashed off and the material was precipitated at pH 2.5-3.0. The ppt was washed 3 times with dilute acetic acid in water. The product was dried under vacuum.

EXAMPLE 14

Di and mono (D) aspartyl mesoporphyrin IX (mixed anhydride method)

200 mg (0.00035 moles of mesoporphyrin IX was dissolved in 100 ml of tetrahydrofuran (THF). 210 μl (0.002 moles) of triethylamine was added with stirring. After 10 minutes, 210 μl (0.0019 moles) of ethylchloroformate was added. After stirring 10 minutes, 50 ml (0.01 moles) of 0.2M KOH containing 500 mg (0.0038 moles) of (D) aspartic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 40-48% methanol in 0.01M KPO$_4$ buffer pH 6.85 (1 liter total volume).

The column effluent was collected via a fraction collector and the tube contents were pooled according to individual components. The order of elution was di (D) aspartyl mesoporphyrin IX, mono (D) aspartyl mesoporphyrin IX, and unsubstituted mesoporphyrin IX.

The methanol was flashed off and the material was precipitated at pH 2.5-3.0. The ppt was washed 3 times with dilute acetic acid in water. The product was dried under vacuum.

EXAMPLE 15

Di and mono (L) glutamyl mesoporphyrin IX (mixed anhydride method 400 mg (0.007 moles) of mesoporphyrin IX was dissolved in 50 ml of tetrahydrofuran (THF). 360 μl (0.0035 moles) of triethylamine was added with stirring. After 10 minutes, 340 μl (0.0031 moles) ethylchloroformate was added. After stirring 10 minutes, 10 ml (0.01 moles) of 1 M KOH containing 543 mg (0.00369 moles) of (L) glutamic acid was added to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 25-60% methanol in 0.01 M KPO$_4$ buffer pH 6.85 (1 liter total volume).

The column effluent was collected via fraction collector and the tube contents were pooled according to individual components. The order of elution was di (L) glutamyl mesoporphyrin IX, mono (L) glutamyl mesoporphyrin IX, and unsubstituted mesoporphyrin IX.

The methanol was flashed off and the material was precipitated at pH 2.5-3.0. The ppt was washed 3 times with dilute acetic acid in water. The product was dried under vacuum.

EXAMPLE 16

Di and mono (D) aspartyl transmesochlorin IX (mixed anhydride method in 1,4 dioxane)

50 mg (0.000087 moles) of transmesochlorin IX was dissolved in 50 ml of 1,4 dioxane. 210 μl (0.002 moles) of triethylamine was added with stirring. After 10 minutes, 210 μl (0.0019 moles) of ethylchloroformate was added. After stirring 10 minutes, 50 ml (0.01 moles) of 0.2M KOH containing 500 mg (0.0038 moles) of (D) aspartic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 40-80% methanol in 0.01M $KPO_4$ buffer pH 6.85 (1 liter total volume).

The column effluent was collected via a fraction collector and the tube contents were pooled according to individual components. The order of elution was di (D) aspartyl transmesochlorin IX, mono (D) aspartyl transmesochlorin IX, and unsubstituted transmesochlorin IX.

The methanol was flashed off and the material was precipitated at pH 2.5-3.0. The ppt was washed 3 times with dilute acetic acid in water. The product was dried under vacuum.

EXAMPLE 17

Di and mono (L) aspartyl transmesochlorin IX (mixed anhydride method in tetrahydrofuran)

135 mg (0.00023 moles) of transmesochlorin IX was dissolved in 100 ml of tetrahydrofuran (THF). 210 μl (0.002 moles) of triethylamine was added with stirring. After 10 minutes, 210 μl (0.0019 moles) of ethylchloroformate was added. After stirring 10 minutes, 50 ml (0.015 moles) of 0.3M KOH containing 750 mg (0.0056 moles) of (L) aspartic acid was added dropwise with stirring to the THF solution. This mixture was stirred 60 minutes at room temperature.

The organic solvent was flashed off and the reaction mixture was checked by silica TLC for product. Benzene/methanol/88% formic acid (8.5/1.5/0.13) was used to develop the chromatogram.

After checking for product, the solution was adjusted to pH 7.5-8.0 and placed on a reverse phase (C-18 silica) column 2.5×30 cm. The reaction mixture was resolved using a linear gradient of 40-80% methanol in 0.01M $KPO_4$ buffer pH 6.85 (1 liter total volume).

The column effluent was collected via a fraction collector and the tube contents were pooled according to individual components. The order of elution was di (L) aspartyl transmesochlorin IX, mono (L) aspartyl transmesochlorin IX, and unsubstituted transmesochlorin IX.

The methanol was flashed off and the material was precipitated at pH 2.5-3.0. The ppt was washed 3 times with dilute acetic acid in water. The product was dried under vacuum.

EXAMPLE 18

(D,L)Aspartylpheophorbide a (carbodiimide method)

55 mg pheophorbide a was dissolved in 10 ml dimethylformamide. 50 mg (D,L) aspartic acid dimethyl ester dihydrochloride was added, then 100 mg of N,N'-dicyclohexyl-carbodiimide was added. The reaction was allowed to stand in the dark at room temperature for 1 hour, then 50 mg more carbodiimide was added. After standing for 1 additional hour, 50 mg more carbodiimide was added and the reaction allowed to stand in the dark for 12 hours at room temperature.

The solvent was removed under vacuum and the product dissolved in 50 ml 1% KOH in methanol with 0.5 ml $H_2O$ and allowed to stand in the dark at room temperature. The course of the hydrolysis is followed by thin layer chromatography (C-18 plates with solvent 75/25 MeOH/.01M pH 6.85 $KPO_4$ buffer).

When hydrolysis of the ester groups is essentially complete, the reaction is terminated by addition of a few drops of glacial acetic acid. The methanol is removed under vacuum and the product is dissolved in 20 ml 0.1 M $NH_4OH$. This solution is placed on a reverse phase (C-18 silica)- column (1.5 cm×30 cm). The elution procedure was a linear gradient from 50 to 80% methanol in 0.01 M $KPO_4$ buffer pH 6.85 (500 ml total volume).

The leading green-gray band contained the (D,L) aspartylpheophorbide a which was collected, flash evaporated to remove methyl alcohol, and precipitated at pH 3. The precipitate was collected and washed 3 times at the centrifuge with dilute acetic acid. The yield of dry product was 27 mg.

EXAMPLE 19

L-Monoaspartyl chlorin $e_6$ (carbodiimide method)

150 mg of chlorin $e_6$ and 250 mg of L aspartic acid di-t.butyl ester hydrochloride were dissolved in 20 ml of dimethyl formamide. There was made a total of 3-100 mg additions of N,N'-dicyclohexyl-carbodiimide at one hour intervals. After 4 hours, the reaction mixture was diluted with 300 ml ether, washed twice with 200 ml $H_2O$ then extracted with 40 ml 1 M KOH. The KOH solution was allowed to hydrolyze overnight, then heated to 70° C. for 10 minutes.

The pH of the solution was adjusted to 7, then any residual ether was removed by flash evaporation. The solution was then applied to a reverse phase (C-18 silica) column (1.5 cm×30 cm). The product was purified by a stepwise elution of methanol/.01 M pH 6.85 $KPO_4$ buffer. Eluted with 5% methanol until unwanted polar pigments were removed. Monoaspartyl chlorin $e_6$ was eluted off with 6-8% methanol, and unreacted chlorin $e_6$ was removed with 25% methanol.

The product was precipitated at pH 3 after flash evaporating briefly to remove methanol, then washed at the centrifuge 3 times with dilute acetic acid.

The product was dried under vacuum. Yield of L-monoaspartylchlorin $e_6$ was 50 mg.

EXAMPLE 20

L Glutamyl chlorin $e_4$ (carbodiimide method)

110 mg chlorin $e_4$ and 220 mg L-glutamic acid dimethyl ester hydrochloride were dissolved in 15 ml of dimethyl formamide. 85 mg of N,N'-dicyclohexyl carbodiimide was then added, and the solution stirred for 1 hour at room temperature. 42 mg more carbodiimide was then added, then 50 mg of carbodiimide was added at 1 hour intervals for two more additions. The reaction mixture was then allowed to stand for 12 hours, one more 50 mg carbodiimide addition was made, and the reaction allowed to stand for 3 hours. Progress of the reaction was followed by reverse phase thin layer chromatography 80% methanol, 20% KPO$_4$ buffer (.01M pH 6.85). A further addition of 50 mg of carbodiimide, with standing, showed no further product formation.

200 ml of ether was added to the reaction mixture, and the ether solution was washed 4 times with water, approximately 100 ml per wash. The ether was then removed by flash evaporation, and the product was dissolved in approximately 25 ml of 3N Hcl. After 48 hours at room temperature, the solution was adjusted to pH3 with NH$_4$OH, and the precipitate was collected and washed at the centrifuge. The product was dissolved in 20% methanol/water with a little NH$_4$OH, and applied to a reverse phase (C-18 silica) column (1.5×30 cm). Elution was continued with 20% MeOH, KPO$_4$ buffer (0.01M pH 6.85). This removed the product (L-Glutamyl chlorin e$_4$). The methanol concentration was increased to remove the unreacted chlorin e$_4$.

The solution was flash evaporated until the methanol was substantially removed, then the products were precipitated at pH3 by addition of Hcl, collected and washed at the centrifuge with dilute acetic acid and dried under vacuum. Yield of mono-L-glutamyl chlorin e$_4$ 21 mg. Yield of recovered chlorin e$_4$ 59 mg.

EXAMPLE 21

L-Monoglutamyl chlorin e$_6$ (carbodiimide method)

130 mg of chlorin e$_6$ and 260 mg L glutamic acid dimethyl ester hydrochloride was dissolved in 18 ml of dimethylformamide. 100 mg of N,N'-dicyclohexylcarbodiimide was added and the reaction mixture stirred for 1 hour. 50 mg more carbodiimide was then added. After 1 hour, the reaction mixture appeared to contain 75-80% of the monosubstituted product by reverse phase TLC (C-18 plates with 70% MeOH, 30% 0.01 M KPO$_4$ pH 6.85). 200 ml Diethyl ether was added, washed twice with 100 ml H$_2$O, then extracted with 30 ml 1 M KOH.

The product was allowed to hydrolyze in the dark in the KOH solution for 12 hours, then was heated to 70° C. for 10 minutes, to complete the hydrolysis of the ester groups. The product was then separated by reverse phase column chromatography (C-18 reverse phase silica 1.5 cm×30 cm), using stepwise gradient elution with methanol in buffer 0.01 M KPO$_4$ pH 6.85. 5% Methanol removed polar impurities. The monoglutamyl chlorin e$_6$ was eluted with 6–8% methanol. Chlorin e$_6$ was eluted off the column with 25% methanol. The methanol was removed by flash evaporation and the L-monoaspartyl chlorin e$_6$ was precipitated at pH 3, collected and washed 3 times at the centrifuge with dilute acetic acid, and dried under vacuum. Yield 40 mg.

EXAMPLE 22

Mono and Di (L) Aspartyl Chlorin e$_6$ (Carbodiimide Method)

400 mg of chlorin e$_6$ and 1 g of L-aspartic acid dibenzyl ester p-tosylate were dissolved in 75 ml of dimethyl formamide. Temperature of the solution was maintained at 65–70° C. with stirring and 100 mg of N,N'-dicyclohexyl carbodiimide was added. (A total of 3 additions were made at 2 hour intervals). The solution was allowed to stir at this tmperature for a total of 20 hrs., then checked by TLC (reverse phase) (C-18 silica) plate, 70% methanol, 30% 0.01 M pH 6.85 KPO$_4$ buffer. The TLC showed greater than 50% monosubstitution with some di-substitution.

150 ml of ether was added, and agitated with 100 ml of water and several drops of glacial acetic acid. The ether phase was separated and the aqueous phase extracted several more times with 100 ml of ether. The ether extracts were combined and washed with water (100 ml) four times to remove dimethyl formamide.

The aspartyl chlorin e$_6$ esters were then extracted into 100 ml of 1 M KOH (4 extractions of 25 ml each). The KOH solution was allowed to stand at ambient temperature for 24 hours to hydrolyze. The components were separated by neutralizing the solution of pH 7 and applying to a reverse phase (C-18 silica) column (1.5 cm×30 cm). The elution was performed using a 1 liter gradient of 30 % methanol to 80% methanol with 0.1 M pH 6.85 KPO$_4$ buffer. Fractions were collected and characterized by TLC. The order of elution was di (L) diaspartyl chlorin e$_6$, L-monoaspartyl chlorin e$_6$ and chlorin e$_6$. Methanol was removed was flash evaporation and the individual components precipitated at pH 3, using HCl.

The products were collected by centrifugation, washed several times with very dilute acetic acid and drived under vacuum. Yield was 23.8 mg.

Physical characteristics of representative compounds (relative polarity) is measured by a standard chromatographic system.

| TLC Plate | Baker Si—Cl8 | 20 um particle size | 200 mm coating thickness | |
|---|---|---|---|---|
| Solven System | 75% methanol | 25% | 0.01 M KPO$_4$ buffer pH 6.85 | |
| Compound | Derivative | $R_f$ | Compound | Derivative | $R_f$ |
|---|---|---|---|---|---|
| Mesoporphyrin IX | — | .32 | Trans-mesochlorin IX | mono(L)glutamyl | .54 |
| Mesoporphyrin IX | mono(D,L)aspartyl | .53 | Trans-mesochlorin IX | di(L)glutamyl | .72 |
| Mesoporphyrin IX | di(D,L)aspartyl | .67 | deuteroporphyrin IX | — | .55 |
| Mesoporphyrin IX | di(D)aspartyl | .66 | deuteroporphyrin IX | mono(D,L)aspartyl | .75 |
| Mesoporphyrin IX | mono(L)aspartyl | .55 | deuteroporphyrin IX | di(D,L)aspartyl | .85 |
| Mesoporphyrin IX | di(L)aspartyl | .66 | deuteroporphyrin IX | mono(L)aspartyl | .75 |
| Mesoporphyrin IX | mono(D,L)glutamyl | .55 | deuteroporphyrin IX | di(L)aspartyl | .84 |
| Mesoporphyrin IX | di(D,L)glutamyl | .72 | protoporphyrin IX | — | .33 |
| Trans-mesochlorin IX | — | .28 | protoporphyrin IX | mono(L)aspartyl | .56 |
| Trans-mesochlorin IX | mono(D)aspartyl | .52 | protoporphyrin IX | di(L)aspartyl | .73 |
| Trans-mesochlorin IX | di(D)aspartyl | .64 | photoprotoporphyrin IX | — | .58 |
| Trans-mesochlorin IX | mono(L)aspartyl | .53 | (isomer mixture) | | |
| Trans-mesochlorin IX | di(L)aspartyl | .64 | photoprotoporphyrin IX | mono(D,L)aspartyl | .78 |
| Hematoporphyrin IX | — | .78 | (isomer mixture) | | |
| Hematoporphyrin IX | mono(D,L)aspartyl | .88 | photoprotoporphyrin IX | di(D,L)aspartyl | .85 |
| Hematoporphyrin IX | di(D,L)aspartyl | .89 | (isomer mixture) | | |

-continued

| TLC Plate | Baker Si—C18 | 20 um particle size | 200 mm coating thickness |
| --- | --- | --- | --- |
| Solven System | 75% methanol | 25% 0.01 M KPO4 | buffer pH 6.85 |

| Compound | Derivative | R_f | Compound | Derivative | R_f |
| --- | --- | --- | --- | --- | --- |
| Chlorin $e_6$ | — | .66 | photoprotoporphyrin IX (isomer mixture) | mono(L)aspartyl | .76 |
| Chlorin $e_6$ | mono(L)aspartyl | .77 | photoprotoporphyrin IX (isomer mixture) | di(L)aspartyl | .85 |
| Chlorin $e_6$ | di(L)aspartyl | .84 | pyropheophorbide a | — | .07 |
| Chlorin $e_6$ | mono(L)glutamyl | .79 | pyropheophorbide a | (D,L)aspartyl | .22 |
| Chlorin $e_4$ | — | .57 | pyropheophorbide a | (L)aspartyl | .23 |
| Chlorin $e_4$ | mono(L)glutamyl | .74 | Mesoporphyrin IX | — | |
| Trans-mesochlorin IX | — | | Mesoporphyrin IX | di(L)glutamyl | .68 |
| Trans-mesochlorin IX | di(D,L)aspartyl | .67 | Mesoporphyrin IX | mono(L)glutamyl | .55 |
| | | | protoporphyrin IX | — | |
| | | | protoporphyrin IX | di(D,L)aspartyl | .70 |
| | | | protoporphyrin IX | mono(D,L)aspartyl | .57 |
| | | | Coproporphyrin III | — | .91 |
| | | | Coproporphyrin III | mono(D,L)aspartyl | .92 |
| | | | Coproporphyrin III | di(D,L)aspartyl | .93 |
| | | | Coproporphyrin III | tri(D,L)aspartyl | .95 |
| | | | Coproporphyrin III | tetra(D,L)aspartyl | .97 |

The visible absorption spectrum in pyridine for all of the aminodicarboxylic acid derivatives are identical to the parent porphyrin, chlorin or bacteriochlorin.

| | Comparative Spectroscopic Absorption Data Solvent in All Cases is P—dioxane. | | | |
| --- | --- | --- | --- | --- |
| Compounds | Absorption Maxima (nm) in Visible Region | mM Extinction Coefficient (EmM) ± 10% | Soret Band nm | nM Extinction Coefficient (EmM) ± 10% |
| Photoprotoporphyrin IX isomer mixture | 668 | 38 | 415 | 180 |
| Pheophorbide a | 667 | 35 | 408.6 | 88 |
| Pyropheophorbide a | 668 | 38 | 411.2 | 89 |
| L-aspartylpyropheophorbide a | 668.5 | 47 | 412.6 | 112 |
| Trans-mesochlorin IX | 643 | 60 | 388 | 183 |
| Di (L) aspartylmesochlorin IX | 643.3 | 53 | 388.6 | 160 |
| Mono (D) aspartylmesochlorin IX | 643.4 | 57 | 388.1 | 165 |
| Mono (L) aspartylmeschllorin IX | 643.6 | 59 | 388.3 | 178 |
| Hematoporphyrin derivative (HPD) | 626 | 2.9 | 399 | 102 |
| Chlorin $e_6$ | 665.6 | 42 | 402 | 124 |
| Mono (L) aspartyl chlorin $e_6$ | 663.5 | 38 | 401.7 | 111 |
| Bacteriopheophorbide a | 753.5 | 44.7 | 359 | 76 |

What is claimed is:

1. A fluorescent mono-, di, tri- or tetramide of an amino acid containing two carboxy groups and a carboxy containing tetrapyrrole compound of the formula:

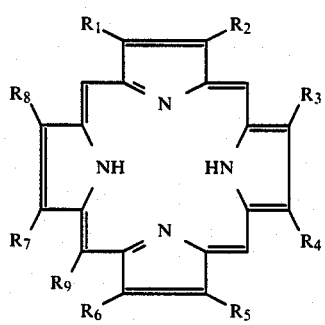

or the corresponding di- or tetrahydrotetrapyrroles, said amide linkage being formed between the amino group of the amino acid and a carboxy-containing substituent attached to the tetrapyrrole; wherein

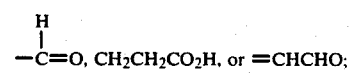

$R_2$ is H, vinyl, ethyl, $-\underset{OH}{CHCH_3}$, acetyl, $\left\{\begin{array}{l}-H\\-ethyl\end{array}\right.$, $-\underset{|}{\overset{H}{C}}=O$, $CH_2CH_2CO_2H$, or $=CHCHO$;

$R_3$ is methyl, $\left\{\begin{array}{l}-H\\-CH_3\end{array}\right.$ or $\left\{\begin{array}{l}-CH_3\\-OH\end{array}\right.$;

$R_4$ is H, vinyl, ethyl, $\underset{OH}{CHCH_3}$, $CH_2CH_2CO_2H$, $=CHCHO$, or $\left\{\begin{array}{l}-H\\-ethyl\end{array}\right.$;

$R_5$ is methyl;
$R_6$ is H, $CH_2CH_2CO_2H$, $CH_2CH_2CO_2R$ or $CO_2H$;

$R_7$ is $CH_2CH_2CO_2H$, $CH_2CH_2CO_2R$ or $\left\{\begin{array}{l}-CH_2CH_2CO_2H\\-H\end{array}\right.$;

-continued

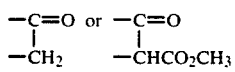

R$_9$ is H, COOH, CH$_2$COOH or methyl;

provided that when R$_1$, R$_2$, R$_3$, R$_4$, R$_7$ and R$_8$ represent two substituents or are divalent and attached to the same carbon, the respective pyrrole ring to which attached is a dihydropyrrole;

R is lower alkyl or benzyl; or

R$_6$ and R$_9$, taken together are $$-\underset{\underset{-CH_2}{|}}{C}=O \text{ or } -\underset{\underset{-CHCO_2CH_3}{|}}{C}=O$$

with the proviso that at least one of R$_1$–R$_9$ includes a free carboxyl group; and salts thereof; with the further proviso that said compound is not mesoporphyrin-bis-L-glutamic acid.

2. The mono- or polyamide according to claim 1 wherein the tetrapyrrole is a porphyrin.

3. The mono- or polyamide according to claim 1 wherein the tetrapyrrole is a chlorin.

4. The mono- or polyamide according to claim 1 wherein the tetrapyrrole is a bacteriochlorin.

5. The amide according to claim 1 wherein the amino acid is an alpha aminodicarboxylic acid.

6. The amide according to claim 1 wherein the amino acid is aspartic acid.

7. The amide according to claim 1 wherein the amino acid is glutamic acid.

8. The compound according to claim 1 which is monoaspartyl trans-mesochlorin IX.

9. The compound according to claim 1 which is diaspartyl trans-mesochlorin IX.

10. The compound according to claim 1 which is monoglutamyl trans-mesochlorin IX.

11. The compound according to claim 1 which is diglutamyl trans-mesochlorin IX.

12. The compound according to claim 1 which is monoaspartyl chlorin e$_6$.

13. The compound according to claim 1 which is triaspartyl chlorin e$_6$.

14. The compound according to claim 1 which is monoglutamyl chlorin e$_6$.

15. The compound according to claim 1 which is diglutamyl protoporphyrin IX.

16. The compound according to claim 1 which is monoaspartyl mesochlorin e$_6$.

17. The compound according to claim 1 which is monoglutamyl protoporphyrin IX.

18. The compound according to claim 1 which is monoaspartyl mesoporphyrin IX.

19. The compound according to claim 1 which is diaspartyl mesoporphyrin IX.

20. The compound according to claim 1 which is diglutamyl mesoporphyrin IX.

21. The compound according to claim 1 which is diaspartyl protoporphyrin IX.

22. The compound according to claim 1 which is monoaspartylbacteriochlorin e$_4$.

23. The compound according to claim 1 which is diaspartyl deuteroporphyrin IX.

24. The compound according to claim 1 which is monoaspartyl deuteroporphyrin IX.

25. The compound according to claim 1 which is monoglutamylbacterioisochlorin e$_4$.

26. The compound according to claim 1 which is diglutamyl deuteroporphyrin IX.

27. The compound according to claim 1 which is mono- or diaspartyl photoprotoporphyrin IX.

28. The compound according to claim 1 which is mono- or diglutamyl photoprotoporphyin IX.

29. The compound according to claim 1 which is mono-, di-, tri- or tetraglutamyl coporphyrin III.

30. The compound according to claim 1 which is mono- or diaspartyl hematoporphyrin IX.

31. The compound according to claim 1 which is mono- or diglutamyl hematoporphyrin IX.

32. The compound according to claim 1 which is mono- or diglutamyl chlorin e$_4$.

33. The compound according to claim 1 which is mono- or diglutamyl mesochlorin e$_4$.

34. The compound according to claim 1 which is mono- or diaspartyl chlorin e$_4$.

35. The compound according to claim 1 which is monoglutamyl deuteroporphyrin IX.

36. A pharmaceutical composition comprising an effective therapeutic amount of a fluorescent mono-, di-, tri- or tetramide of an amino acid containing two carboxy groups and a carboxy containing tetrapyrrole compound of the formula:

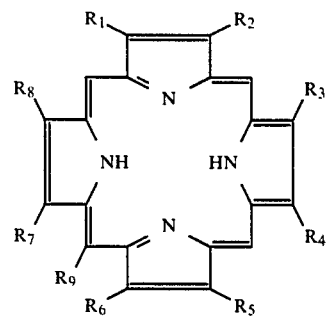

or the corresponding di- or tetrahydrotetrapyrroles, said amide linkage being formed between the amino group of the amino acid and a carboxy-containing substituent attached to the tetrapyrrole; wherein $$R_1 \text{ is methyl, } \begin{cases} -H \\ -CH_3 \end{cases} \text{ or } \begin{cases} -OH \\ -CH_3 \end{cases}$$

$$R_2 \text{ is H, vinyl, ethyl, } -\underset{\underset{OH}{|}}{C}HCH_3, \text{ acetyl, } \begin{cases} -H \\ -ethyl \end{cases},$$

$$-\underset{\underset{}{|}}{\overset{H}{C}}=O, CH_2CH_2CO_2H, \text{ or } =CHCHO;$$

$$R_3 \text{ is methyl, } \begin{cases} -H \\ -CH_3 \end{cases} \text{ or } \begin{cases} -CH_3 \\ -OH \end{cases};$$

R$_4$ is H, vinyl, ethyl, $\underset{\underset{OH}{|}}{C}HCH_3$, $$CH_2CH_2CO_2H, =CHCHO, \text{ or } \begin{cases} -H \\ -ethyl \end{cases};$$

$R_5$ is methyl;

$R_6$ is H, $CH_2CH_2CO_2H$, $CH_2CH_2CO_2R$ or $CO_2H$;

$R_7$ is $CH_2CH_2CO_2H$, $CH_2CH_2CO_2R$ or $\begin{cases} -CH_2CH_2CO_2H \\ -H \end{cases}$;

$R_8$ is methyl or $\begin{cases} -CH_3 \\ -H \end{cases}$ $R_9$ is H, COOH, $CH_2COOH$ or methyl;

provided that when $R_1$, $R_2$, $R_3$, $R_4$, $R_7$ and $R_8$ represent two substituents or are divalent and attached to the same carbon, the respective pyrrole ring to which attached is a dihydropyrrole;

R is lower alkyl or benzyl; or $R_6$ and $R_9$ taken together are $\begin{matrix} -C=O \\ | \\ -CH_2 \end{matrix}$ or $\begin{matrix} -C=O \\ | \\ -CHCO_2CH_3 \end{matrix}$ with the proviso that at least one of $R_1-R_9$ includes a free carboxyl group;

and pharmaceutically acceptable salts thereof, and a pharmaceutically acceptable carrier therefor.

37. The composition according to claim 36 wherein the amino acid is an alpha aminodicarboxylic acid.

38. The composition according to claim 37 wherein the tetrapyrrole is a chlorin.

39. The composition according to claim 37 wherein the tetrapyrrole is a bacteriochlorin.

40. The composition according to claim 37 wherein the tetrapyrrole is a porphyrin.

41. The composition according to claim 37 wherein the amino acid is aspartic acid.

42. The composition according to claim 37 wherein the amino acid is glutamic acid.

* * * * *

UNITED STATES PATENT AND TRADEMARK OFFICE
CERTIFICATE OF CORRECTION

PATENT NO. : 4,675,338

DATED : June 23, 1987

INVENTOR(S) : Bommer, et al.

It is certified that error appears in the above-identified patent and that said Letters Patent is hereby corrected as shown below:

Column 26, Line 25, delete "$R_1$ is methyl, $\begin{cases} -H \\ -CH_3 \end{cases}$ or $\begin{cases} -OH \\ -CH_3 \end{cases}$"

Column 26, Line 45, add --$R_1$ is methyl, $\begin{cases} -H \\ -CH_3 \end{cases}$ or $\begin{cases} -OH \\ -CH_3 \end{cases}$--

Signed and Sealed this

Fifth Day of April, 1988

Attest:

DONALD J. QUIGG

*Attesting Officer*   *Commissioner of Patents and Trademarks*